(12) United States Patent
Mandell et al.

(10) Patent No.: US 12,715,142 B2
(45) Date of Patent: Aug. 25, 2026

(54) AUTOMATED ROBOTIC ROD BENDER

(71) Applicant: GLOBUS MEDICAL, INC., Audubon, PA (US)

(72) Inventors: Douglas Mandell, Wakefield, MA (US); David C. Paul, Phoenixville, PA (US); Norbert Johnson, North Andover, MA (US); David Cleary, Dracut, MA (US); Danielle Reinhard, Lafayette Hill, PA (US)

(73) Assignee: Globus Medical, Inc., Audubon, PA (US)

( * ) Notice: Subject to any disclaimer, the term of this patent is extended or adjusted under 35 U.S.C. 154(b) by 110 days.

(21) Appl. No.: 18/769,642

(22) Filed: Jul. 11, 2024

(65) Prior Publication Data

US 2026/0014711 A1 Jan. 15, 2026

(51) Int. Cl.

*B25J 11/00* (2006.01)
*A61B 34/30* (2016.01)
*B25J 15/00* (2006.01)

(52) U.S. Cl.

CPC ............. *B25J 11/005* (2013.01); *A61B 34/30* (2016.02); *B25J 15/0019* (2013.01); *B25J 15/0085* (2013.01)

(58) Field of Classification Search

CPC ........... A61B 17/70–7091; A61B 34/30; B25J 11/005; B25J 11/0019; B25J 11/0085
See application file for complete search history.

(56) References Cited

U.S. PATENT DOCUMENTS 1,068,626 A 7/1913 Buck
4,737,038 A 4/1988 Dostoomian
4,757,710 A 7/1988 Haynes
5,129,388 A * 7/1992 Vignaud ............ A61B 17/7004 606/258
6,058,820 A * 5/2000 Rinner ................. B23D 29/023 83/633
8,556,807 B2 10/2013 Scott et al.
9,005,113 B2 4/2015 Scott et al.
9,271,633 B2 3/2016 Scott et al.
9,565,997 B2 2/2017 Scott et al.
9,962,069 B2 5/2018 Scott et al.
11,510,733 B1 * 11/2022 Roh ....................... A61B 34/32
2011/0054535 A1 * 3/2011 Gephart ............. A61B 17/7025 606/279
2011/0301646 A1 * 12/2011 Kretzer ............. A61B 17/7037 606/279

(Continued)

*Primary Examiner* — Nicholas J Plionis

(57) ABSTRACT

Instruments, systems, and methods for automated rod bending. The automatic rod bending system integrates seamlessly with a multi-arm surgical robotic system. A powered holding end effector may be coupled to a first surgical arm and a powered bending end effector may be coupled to a second surgical arm of the surgical robotic system. The holding end effector may include a feeder roller configured to advance the rod and a rotation roller configured to rotate the rod about its longitudinal axis. The bending end effector coupled may include a fixed mandrel and a movable mandrel configured to bend the rod to a prescribed bending profile. The powered end effectors may be synchronized to ensure the bends are made at correct locations and directions for a customized patient specific rod.

19 Claims, 8 Drawing Sheets

(56) References Cited

U.S. PATENT DOCUMENTS

| | | | | |
|---|---|---|---|---|
| 2014/0311203 | A1* | 10/2014 | Crawford | B21D 7/08<br>72/169 |
| 2018/0228351 | A1 | 8/2018 | Scott et al. | |
| 2018/0303552 | A1* | 10/2018 | Ryan | A61B 17/7002 |
| 2020/0015858 | A1* | 1/2020 | Paster | A61B 34/10 |

* cited by examiner

AUTOMATED ROBOTIC ROD BENDER

FIELD OF THE INVENTION

The present disclosure relates to instruments, systems, and methods for automated robotic bending of a rod for spinal surgeries.

BACKGROUND OF THE INVENTION

Computer-assisted technology may be used during spine surgery to allow surgeons to accurately and repeatably place implant hardware with decreased intraoperative radiation and operative time as opposed to conventional surgical techniques. During spinal procedures with screw fixation, one or more spinal rods may be placed as the final step to achieve correction. In some cases, the spinal rod(s) are bent to match the screw locations and the contours of the patient's spinal anatomy.

Rod bending may include intraoperative manual bending with a combination of French benders, table benders, and in situ benders. Unfortunately, surgeons can experience physical and cognitive load when manually bending a rod to the desired location. The bends can be complicated and challenging to match the left and right sides of the construct. The process is often time-consuming and can result in high stress areas on the rod, which may lead to potential increased risk of failure. Some other rod benders require a separate unit brought into the operating room or a plan created before the case so the patient specific rod can be developed offsite and then shipped to the surgeon for use during the case.

Thus, there remains a need for an intraoperative, streamlined rod bending platform that can efficiently and effectively execute a plan without additional equipment in the operating room.

SUMMARY OF THE INVENTION

To meet this and other needs, instruments, systems, and methods for automated robotic bending are provided. In particular, the spinal rod may be contoured into a complex three-dimensional (3D) shape to match the patient's spine, align with and seat in screw heads fixed to the spine, and/or be deformable to achieve the desired correction when corrective forces are applied. The rod bender system may include specialized end effectors attachable to a surgical robotic system with multiple surgical arms and integrated navigation. The specialized end effectors may be attached to each surgical arm to perform separate functions. A first end effector may be configured for holding the spinal rod for feeding and cutting the rod, and a second end effector may be configured for bending the spinal rod. The end effectors work in concert to bend and contour the rod into its desired shape. The rod bender system may be controllable by the surgical robotic system and/or with navigated assistance. Furthermore, the robotic system may be used to generate an intraoperative rod plan before or during the operation, for example, based on screw placement and/or user input. The rod plan may automatically produce patient specific rods meeting the planned alignment goals during the procedure in real-time.

According to one embodiment, an automatic rod bending system includes a multi-arm surgical robotic system, a powered holding end effector, and a powered bending end effector. The multi-arm surgical robotic system has a movable base station including an on-board computer, a display electronically coupled to the computer, a machine vision camera electronically coupled to the computer, and first and second surgical arms electronically coupled to the computer and movable based on commands processed by the computer. The powered holding end effector is coupled to the first surgical arm. The holding end effector has a housing defining a channel for receiving a rod therethrough, a feeder roller located adjacent to the channel such that an edge of the feeder roller is configured to contact the rod to advance the rod through the channel, and a rotation roller located adjacent to the channel such that an edge of the rotation roller is configured to rotate the rod about its longitudinal axis. The rotation roller is positioned perpendicular to the feeder roller. The powered bending end effector is coupled to the second surgical arm. The bending end effector has a housing with a fixed mandrel and a movable mandrel such that when the rod is positioned therebetween, the movable mandrel is configured to apply a force to bend the rod. Movements of the holding end effector and the bending end effector synchronize to ensure bends are made at correct locations and directions for a customized patient specific rod.

The automatic rod bending system may include one or more of the following features. The holding end effector may include cutoff shears located at an exit of the channel. The cutoff shears may include a pair of blades that slide past each other to automatically cut the rod to a desired final length. The holding end effector may include a notch cutter with a cutting head configured to notch the rod. The bending end effector may include an upper arm and a lower arm with a fixed center post located at a pivot of the upper and lower arms, and one or both of the arms may include a jaw on a distal end, such that the rod is positionable between the fixed center post and the jaw. The upper and lower arms may be automatically controlled by a motor driven lead screw. The motor driven lead screw may interact with a captive lead nut to move the upper arm relative to the lower arm. A proximal end of the lower arm may rest in a groove in the housing of the bending end effector in a fixed position, and a proximal end of the upper arm may interface with the captive lead nut such that when the captive lead nut travels downward, the nut forces the upper arm downward, thereby applying a bending force to the rod. The bending end effector may include a pair of fixed mandrels and the movable mandrel may be configured to travel along a slit in the housing. The slit may be oriented perpendicular to the longitudinal axis of the rod when positioned between the fixed and movable mandrels. The holding and bending end effectors may be powered by one or more electric motors, which are controlled by the robotic system.

According to one embodiment, a process workflow for intraoperative rod bending may include: (a) planning screw location and rod geometry using a surgical robotic system, for example, having a machine vision camera; (b) simulating spinal correction using the surgical robotic system to determine a prescribed bending profile for a rod based on proposed or current screw locations; (c) outputting rod diameter and initial rod length defined by the surgical robotic system to a user; (d) inserting a rod blank into a powered holding end effector having a housing defining a channel for receiving the rod blank therethrough, a feeder roller for advancing the rod blank through the channel, and a rotation roller for rotating the rod blank about its longitudinal axis; (c) automatically feeding and rotating the rod blank through a powered bending end effector having a housing with a fixed mandrel and a movable mandrel with the rod blank positioned therebetween, and moving the movable mandrel to bend the rod blank to the prescribed bending profile for the rod; and (f) automatically cutting the rod to length by the powered holding end effector. The entire process may be continuously monitored by the machine vision camera to ensure that the rod is formed according to the prescribed bending profile. The rod bending may occur intraoperatively during surgery. The robotic system may be configured to make automated, on-the-fly, corrections throughout the process. The process may also include installing screws with the surgical robotic system. The planning and simulation steps may be iterative until final screw placements are made. The process may also include notching the rod with the powered holding end effector. The process may also include replacing one or both of the end effectors to perform different functions during the surgical procedure.

According to one embodiment, an automatic rod bending system for use with a multi-arm surgical robotic system with machine vision monitoring and verification may include a powered holding end effector coupled to a first surgical arm and a powered bending end effector coupled to a second surgical arm of the multi-arm surgical robotic system. The holding end effector may have a housing defining a channel extending from an entry point to an exit point for receiving a rod therethrough along a longitudinal rod axis, a feeder roller located adjacent to the channel such that an edge of the feeder roller is configured to automatically advance the rod through the channel, a rotation roller located adjacent to the channel such that an edge of the rotation roller is configured to automatically rotate the rod about the rod axis, wherein the rotation roller is positioned perpendicular to the feeder roller, a notch cutter positioned beneath the rotation roller and adjacent to the channel such that a cutting head of the notch cutter is configured to automatically notch the rod, and cutoff shears located near the exit point of the channel to automatically cut the rod to a desired length. The powered bending end effector may have a housing and a pair of bender arms with a fixed center post located at a pivot of the bender arms, one or more jaws mounted on distal ends of the bender arms, and a motor driven lead screw which interacts with a captive lead nut to move one of the bender arms. The rod is positionable between the fixed center post and the one or more jaws along the rod axis, and application of force to the bender arms causes the one or more jaws to orbit about the center post, thereby applying a bending force to the rod. Alternatively, the powered bending end effector may be substituted with a compact bender having a pair of fixed mandrels and a movable mandrel, which travels along a slit, to apply a bending force to the rod. The rod may be configured to be automatically fed, rotated, and bent into a complex three-dimensional geometry based on a planned and simulated intraoperative rod plan from the surgical robotic system, to thereby produce a customized patient specific rod in real-time.

Also provided are kits including implants including rods of varying types and sizes, instruments, and other components for performing the procedures.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

Embodiments of the disclosure are generally directed to instruments, systems, and methods for automatic robotic rod bending of a rod for spinal surgeries. In particular, a rod bender system can be utilized to shape a spinal rod into a complex three-dimensional (3D) configuration that conforms to the patient's spinal curvature, aligns with and fits into screw heads attached to the spine, and is adaptable to achieve the necessary adjustments when corrective forces are applied. The rod bender system may include specialized end effectors, including a separate holder and bender, each attachable to surgical arms of a surgical robotic system. The holding end effector may be configured for holding, feeding, notching, and/or cutting the rod, and the bending end effector may be configured for bending the spinal rod. The end effectors work cooperatively and are controllable by an automated robot system with navigated surgical assistance, or by other suitable robotic system(s).

The surgical robotic system may be configured for full navigation and accurate alignment during spine surgery. The surgical robotic system may allow for locating anatomical structures in open or minimally invasive surgical (MIS) procedures and navigation of surgical instruments and devices in real-time. Different end effectors may be attached to the surgical arms to perform different functions. For example, the surgical arms and attached end effectors may be used during spinal surgery to position and install pedicle screws and/or interbody implants, automatically contour and cut the spinal rod, install the spinal rod, or perform other surgical tasks. It will be appreciated that the end effectors may be swapped or replaced, as needed, on the ends of the surgical arms depending on the desired functionality throughout the surgical process. Although generally described with reference to performing spinal surgery, it will be appreciated that the systems and methods described herein may be applied to other orthopedic locations in the body as well as other medical procedures, such as trauma applications, cranial procedures, and oncology applications.

Figure 1:
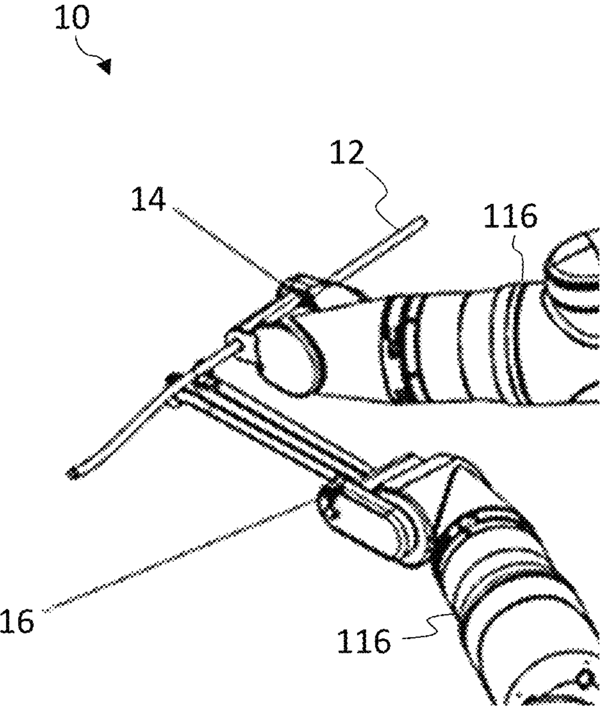
FIG. 1 illustrates a close-up view of an integrated rod bender surgical robotic system with a holding end effector attached to a first surgical arm and a bending end effector attached to a second surgical arm, which work together to bend the spinal rod according to one embodiment.

Turning now to the drawing, FIG. 1 illustrates an integrated rod bending surgical robotic platform 10 according to one embodiment. The rod bending platform 10 is configured for automated robotic bending of a spinal rod 12 utilizing specialized end effectors 14, 16, which are controllable by one or more surgical robots and/or navigation systems, such as multi-arm robot system 100 described in more detail for FIG. 2. For automated rod bending, unique purpose-specific rod bending end effectors 14, 16 may be fitted to each arm 116 of the multi-arm surgical robot system 100. A first end effector 14 may be configured to hold, feed, and/or cut the rod 12, and the second end effector 16 may be configured to bend and contour the rod 12. The first and second end effectors 14, 16 work cooperatively to shape and size the spinal rod 12, thereby providing a customized rod 12 in real-time for the individual patient. The entire fabrication process may be planned within and executed by the surgical robotic system 100 and monitored by the machine vision system. The integrated rod bender system 10 leverages the platform-based multiple robotic arms 116 with machine vision and augments this technology with purpose-built end effectors 14, 16 to enable a seamless, verifiable, rod bending process for rods 12 of any size and degree of complexity.

Spinal rods 12 are used in surgical procedures to stabilize the spine, correct deformities, and maintain proper alignment of the spine. The spinal rod 12 may be an elongated shaft having a generally cylindrical outer body. It will be appreciated that the spinal rod 12 may also have other cross-sectional shapes, such as oval, rectangular, or flattened surfaces. The rod 12 may be made from biocompatible materials, such as titanium, titanium alloys, cobalt-chrome alloys, or stainless steel, that have high tensile strength and can withstand forces and stresses placed on the spine. The rods 12 may range in diameter (e.g., 3 mm-6 mm) and length (e.g., ranging from 10 cm to upwards of 50 cm) depending on the number of vertebral levels that need to be spanned. The choice of rod type, size, and material may be influenced by the specific surgical goals, the patient's anatomy, and the surgeon's preference. During the surgery, the surgeon may need to bend the rod 12 to match the patient's spinal curvature, to align with new or existing hardware, such as screw or tulip heads, and/or to achieve the desired correction when corrective forces are applied to the rod 12. In surgeries for conditions like scoliosis or kyphosis, the rods 12 may be bent to correct abnormal curvatures, to realign the spine, and to act as a brace to maintain the spine in its new corrected position. In stabilization procedures, the rods 12 provide the necessary stability to the affected segments of the spine. For spinal fusion, the rods 12 help to maintain proper alignment of the spine while the vertebrae fuse together. Examples of bone fasteners, other implants, and rod constructs are described in more detail, for example, in U.S. Pat. No. 10,603,081, which is incorporated by reference herein in its entirety for all purposes. The rod bending platform 10 may be used to bend, contour, and/or shape the rod 12 to achieve the desired curvature and alignment in real-time.

Figure 2:
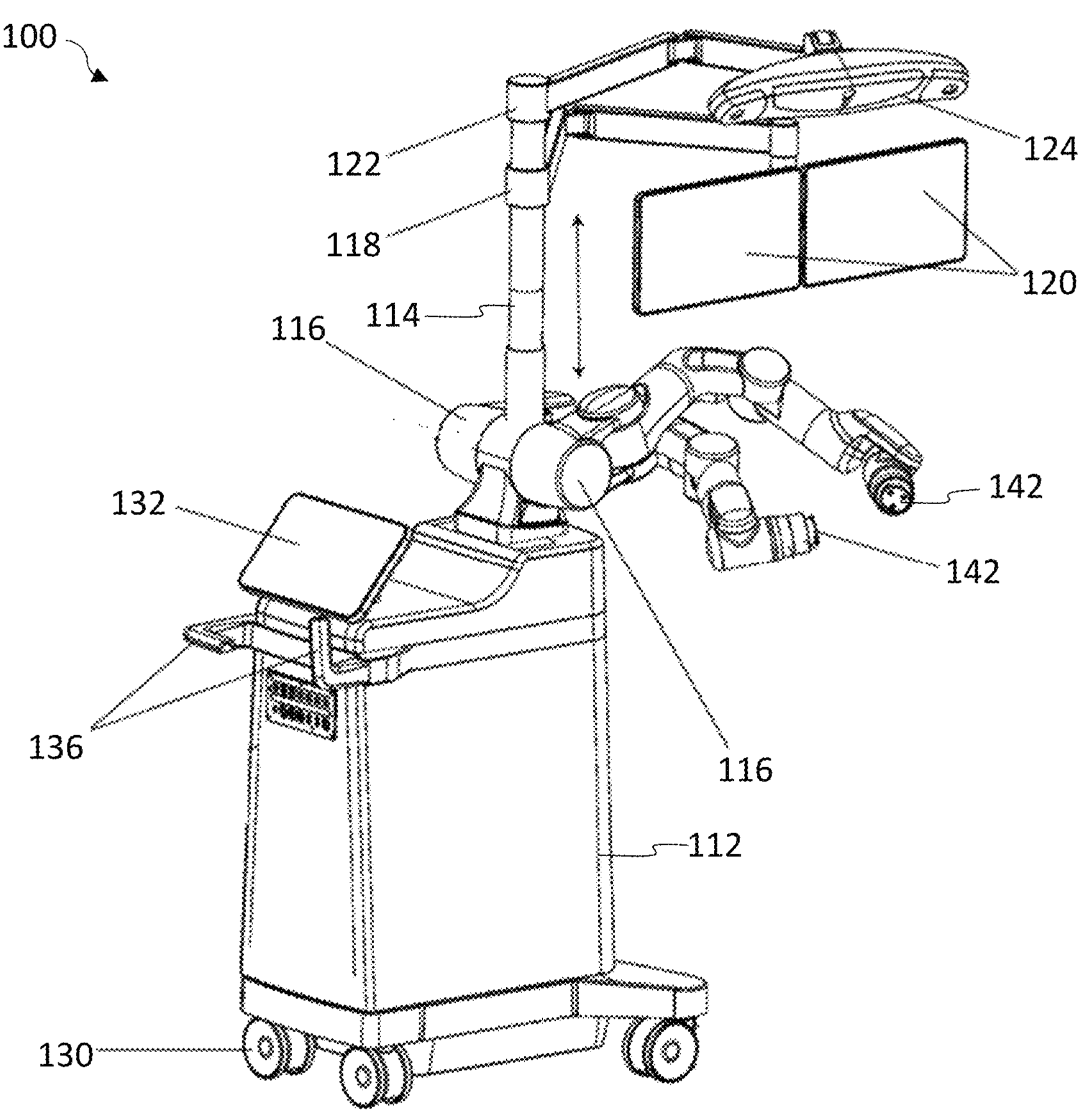
FIG. 2 shows a surgical robotic system having two surgical arms in accordance with one embodiment.

In one embodiment, multi-arm surgical robot and/or navigation system 100 may be used to automate the rod bending process. FIG. 2 illustrates one example of a multi-arm surgical robotic and navigation system 100. Surgical robotic system 100 may include, for example, a movable robotic base station 112 on wheels 130, a vertical arm positioner 114 attached to the base station 112, and multiple arms 116, 118, 122 attached to the positioner 114. Two or more surgical arms 116 may help to guide instruments or perform surgical tasks, for example, using end effectors attachable to an end effector interface 142 at the distal end of each arm 116. A monitor arm 118 is configured for supporting one or more displays or monitors 120 (e.g., a dual touch screen display). A camera arm 122 is configured for supporting one or more navigation and/or machine vision cameras 124 or other advanced sensing technologies. The navigation or machine vision cameras 124 may be configured to monitor, track, and analyze the position and movement of the surgical arms, end effectors, instruments, implants, and/or other objects in the camera's field of view in real-time. The cameras 124 may include navigation cameras which monitor active or passive tracking markers (e.g., fiducials) and/or machine vision cameras which monitor objects, machine vision markings, or other optical tracking techniques. The base 112 may support a cabinet-mounted display or terminal 132 and includes handles 136 for transporting and positioning the system 100. Further details on the multi-arm robotic system 100 are provided in U.S. patent application Ser. No. 18/603,494, which is incorporated by reference herein in its entirety for all purposes. Additional examples of surgical robotic and/or navigation systems can also be found, for example, in U.S. Pat. Nos. 10,675,094 and 9,782,229, which are incorporated by reference herein in their entireties for all purposes.

The base station 112 houses an on-board computer or computing unit for controlling all functionality of the robotic system 100. The on-board computer may include a central processing unit (CPU), memory, and an input/output interface. The central processing unit carries out the instructions of a computer program or software by performing arithmetical, logical, control, and input/output (I/O) operations specified by the instructions. The memory may include volatile and non-volatile memory storage that temporarily or permanently store data and instructions that are currently in use or will be needed by the central processing unit. This may include, for example, random access memory (RAM), read-only memory (ROM), and storage devices like hard drives. It will be appreciated that tangible/non-transitory computer-readable medium comprising software code or storing instructions executable by one or more processors may be adapted, when executed on a data processing apparatus, to perform any computer method set out herein. The input/output interface allows the computer system to interact with the user, take in information, and deliver results, and may include devices such as a monitor, keyboard, mouse, network interface for internet connectivity, and so forth. Although an on-board computer is exemplified herein, it will be appreciated that the computer or one or more functions may be replaced or supplemented with external devices or systems (e.g., cloud computing).

Each surgical arm 116 may be configured to perform a wide range of motions and adjustments, for example, mimicking the movements of the human arm, hand, and/or fingers and closely replicating the dexterity and precision of a skilled surgeon. In one embodiment, the surgical arms 116 include a pair of left and right surgical arms arranged about the bottom of the arm positioner 114. Each surgical arm 116 may include a plurality of arm segments or links interconnected by various types of joints. Each joint may allow for specific types of movement or offer specialized motion. The joints may include rotary joints, prismatic joints, spherical joints, universal joints, cylindrical joints, planar joints, or other suitable joints that contribute to the arm's range of motion, flexibility, and reach. In the embodiment shown, the system 100 includes left and right surgical arms 116, which each allow for movement with seven degrees of freedom (7 DoF). For example, the movement may include three translational movements (along the x, y, and z axes), three rotational movements (around the x, y, and z axes), and an additional rotation or translation for imparting high precision and dexterity. It will be appreciated that the surgical arms 116 may be configured to have any suitable orientation or movement allowing each arm 116 to move forward/ backward, left/right, up/down, yaw left/right, pitch tilt up/down, roll around its own axis, or otherwise translate or rotate for complex movement. The surgical arms 116 may be configured with zero backlash to ensure the movements are highly precise, accurate, and directly reflective of the surgeon's commands without any delay.

Figure 3:
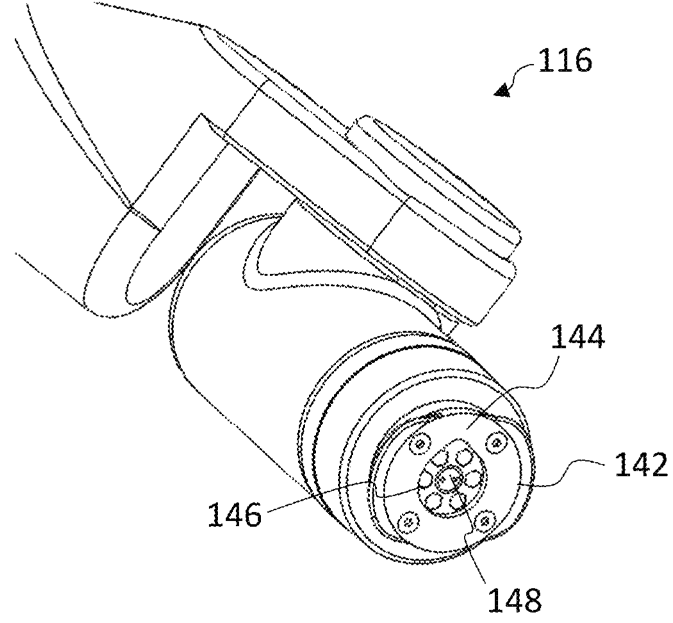
FIG. 3 shows a close-up view of the end effector interface at a distal end of the surgical arm according to one embodiment.

With further reference to FIG. 3, the distal end of each surgical arm 116 includes an end effector interface 142 for securing the end effector 14, 16 to the end of the surgical arm 116. In addition to rod bending end effectors 14, 16, the end effector may include any device or tool which attaches to the end of the robotic surgical arm 116 to interact with the surgical site. In some cases, the end effector may include a guide tube to provide precise positioning of instruments placed therethrough. In other cases, the end effector may include an active or workable instrument, such as a retractor for retracting soft tissues, which is controlled by the system 100 or manually. Each end effector may be provided as a separate component, which is sterilized prior to use. The end effector interface 142 may include mechanical and/or electronic coupling of the end effector to the distal end of the surgical arm 116. For example, the end effector interface 142 may include a mounting flange 144 with a conducive pad 146 for electrical connection and a ferrous target 148 for magnetic connection. It will be appreciated that the end effector interface 142 may be configured in any suitable manner as a power and communication interface for each end effector, and which allows for a rigid connection of each end effector to the surgical arm 116 through the sterile drape.

The first end effector 14 may be configured to hold, feed, and/or cut the rod 12. At its most basic functionality, the first end effector 14 may be configured to securely hold the rod being bent, for example, using an arm-mounted clamp or collet. In this embodiment, the holding end effector 14 can leverage the dexterity and functionality of the robotic arm 116 for all axial moves and rotations required to feed the rod blank through the bending apparatus, such as a French bender. A basic holding end effector 14 may minimize the complexity of the overall system while securely holding the rod 12 for bending.

In another embodiment, the first end effector 14 may be configured to hold and feed the rod 12 through the bending apparatus. In this embodiment, the first end effector 14 may include one or more feeders or rollers configured to feed and/or rotate the rod 12. The feeder roller(s) grip the spinal rod 12 and move it linearly into the bending apparatus. The feeder carefully advances the rod 12 into the bending operation at a controlled and precise speed. The rotation roller(s) rotate the rod around its longitudinal axis to thereby achieve bends in multiple planes and accommodate the complex three-dimensional rod shape. The rotation roller(s) enable the rod 12 to be turned to the correct orientation before and during the bending process. The synchronization of feeding and rotation ensures the bends are made at the correct locations and directions to provide the customized rod 12. Cutoff may be a separate operation external to the bending workflow.

Figure 4:
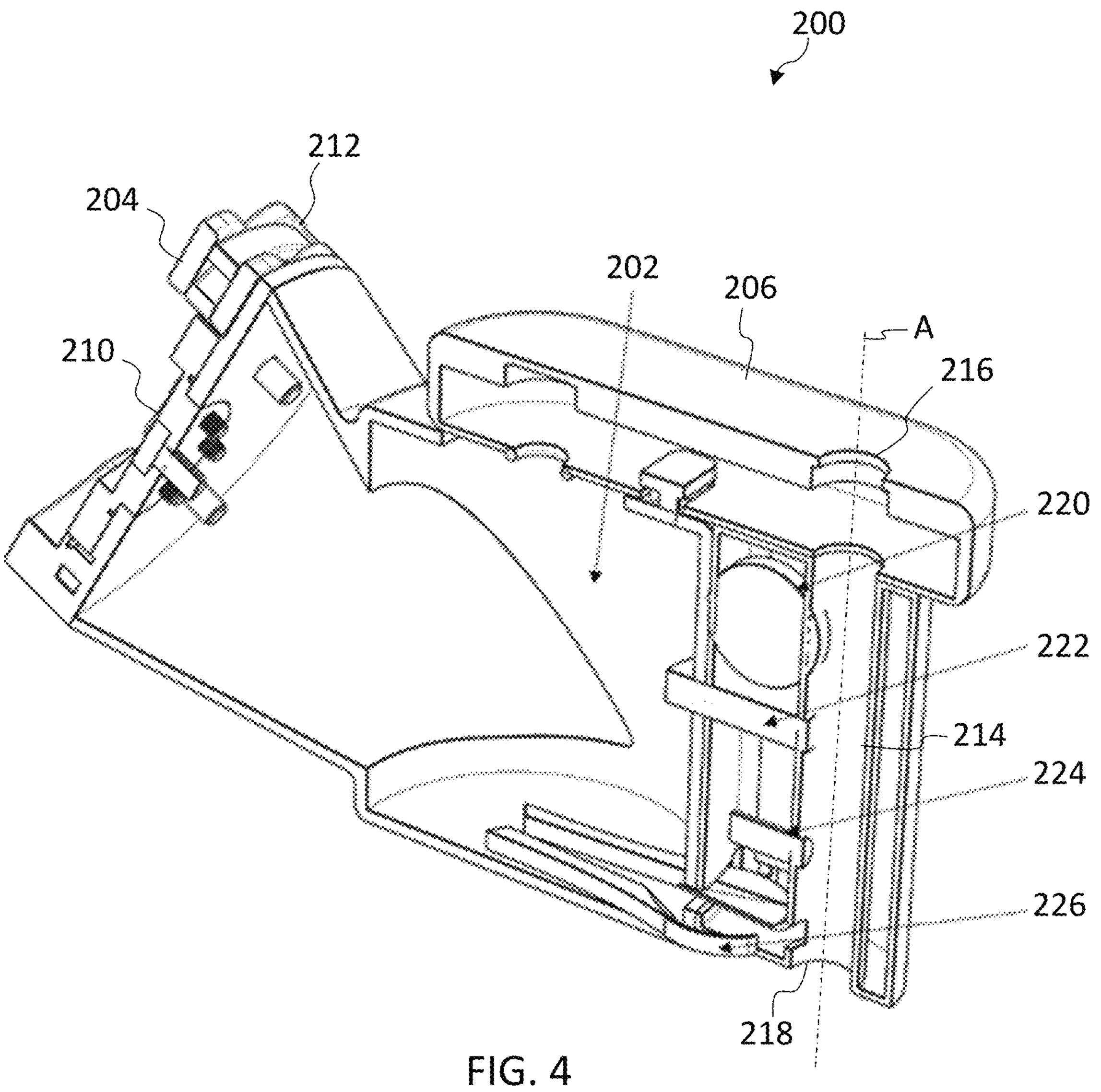
FIG. 4 shows a cross-section of a powered holding end effector configured for feeding, notching, and cutting the spinal rod according to one embodiment.

In yet another embodiment, the first end effector 14 is configured to incorporate holding, feeding, and cutting operations in a single unit. FIG. 4 depicts one example of an automated holding end effector 200 configured for automatically feeding and cutting the spinal rod 12. This configuration may help to alleviate the surgeon's physical workload by automating rod bending and supporting end preparation and cutoff. Furthermore, direct manipulation of the rod 12 during bending may provide robotic kinematic benefits. The movements of linear feed and axial rotation, when applied co-axially to the rod 12, may be much simpler than achieving those same movements through the 7 DOF robot arm 116 which involves complex multi-axis movements.

As best seen in FIG. 4, the holding end effector 200 may include a mechanism housing 202 with an attachment portion 204 and a rod portion 206. The attachment portion 204 may include an arm attachment interface 210 configured to mate with the end effector interface 142 of the surgical arm 116. The arm interface 210 may include a complementary mounting flange with electrical and magnetic connections, which mates with the end effector interface 142. The end effector 200 may be coupled via a clamp 212, for example, including a spring-loaded clip that clamps the end effector 200 to the surgical arm 116. One example of a clamp for mechanically and electronically coupling the robot arm to the end effector is described in further detail in U.S. Pat. No. 11,684,437, which is incorporated by reference herein in its entirety for all purposes.

The rod portion 206 of the housing 202 may include a rod pass-thru or channel 214 sized and dimensioned to receive the spinal rod 12 therethrough. The rod channel 214 may include a cylindrical continuous passage or through bore having an entry 216 and an exit 218. The axis of the rod opening 214 may coincide with the longitudinal axis A of the rod 12 when positioned therethrough. The channel 214 serves as a guide for the rod 12 ensuring that the rod 12 maintains a straight trajectory as the rod 12 passes through the channel 214.

A feeder roller 220 may be located adjacent to the channel 214 and toward the entry 216 of the channel 214. An edge of the roller 220 may contact the rod 12 in order to grip and advance the rod 12 through the channel 214. The feeder roller 220 may have a cylindrical body with a round cross-section to allow for even contact and consistent force against the rod 12. The edge of the feeder roller 220 may include a smooth surface, a textured surface, or a coated surface to enhance grip and prevent slippage of the rod 12. The feeder roller 220 may be adjustable to control pressure applied to the rod 12. As the feeder roller 220 rotates, for example, with a clockwise rotation, the roller 220 exerts a controlled force onto the rod 12, thereby pushing the rod 12 through the channel 214.

A rotation roller 222 may be located beneath the feeder roller 220 and next to the rod channel 214. The rotation roller 222 may also have a cylindrical body with a round cross-section configured to rotate the rod 12 about its longitudinal axis A. The rotation roller 222 may be set perpendicular to the feeder roller 222 to turn the rod 12 to the correct orientation to achieve multi-directional bends. The edge of the rotation roller 222 may contact the rod 12 to rotate the rod 12 to its desired position. The rotation roller 222 may be configured to rotate in one or both directions, and may be adjustable to regulate the pressure exerted on the rod 12.

The rollers 220, 222 may be powered by one or more electric motors (e.g., AC, DC, servo, stepper) or pneumatic system (not shown) to provide consistent and adjustable feed rates. The motors may be contained within the housing 202, within the surgical arms 116, or otherwise configured to control movement of the rollers 220, 222. The motion of the feeder and rotation rollers 220, 222 may be coordinated to synchronize the speed and direction of the rollers 220, 222. Alternatively, the feeder and rotation rollers 220, 222 may be combined into a duplex threadless lead screw assembly or other suitable feeding configuration. Although a specific configuration of rollers 220, 222 is shown, it will be appreciated that the number, type, size, location, and orientation of the rollers 220, 222 may be modified to optimize the feeding and rotation performance.

The end effector 200 may include a notch cutter 224 configured to make precise notches or grooves in the rod 12. The notch cutter 224 may be located beneath the rotation roller 222 and positioned next to the rod channel 214 such that a cutting tip or cutting head is configured to notch the rod 12 at a given location. The cutting tip may be configured to form a square or rectangular notch, V-shaped or U-shaped notch, or custom shape tailored to the implant system. The notch cutter 224 may include adjustable depth and/or width settings to allow for further customization of the resulting notch.

The end effector 200 may include cutoff shears 226 located near the exit 218 of the rod channel 214. The cutoff shears 226 may include a pair of blades that slide past each other in a scissor-like action to apply a cutting force to cut the rod 12 to length. The shears 226 may provide for immediate and automatic cutting of the rod 12 to the desired length once the rod 12 is fed to the correct position. Sensors may be used to detect the position of the rod 12 and trigger the shears 226 to achieve the desired final length. The notch cutter and shears 224, 226 may be mechanically, hydraulically, or pneumatically operated. The notch cutter and shears 224, 226 may be controlled by motors or actuators contained within the housing 202 or another suitable location. The notch cutter and shears 224, 226 may be synchronized with the feeding and rotation operations to optimize fabrication of the rod 12.

Figure 5:
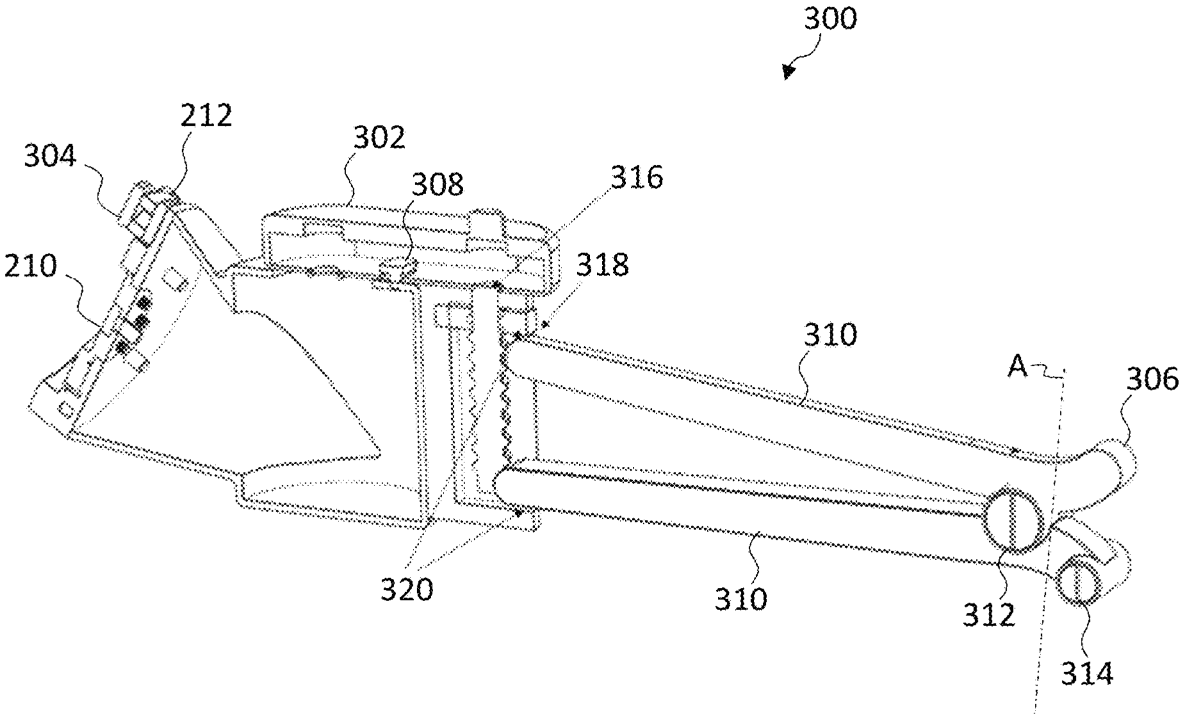
FIG. 5 shows a cross-section of a powered bending end effector configured for bending the spinal rod according to one embodiment.

The second end effector 16 may be configured to bend and contour the rod 12. In its simplest form, the second end effector 16 may be configured to bend the rod 12 as it is fed therethrough. Similar to the holding end effector 14, the bending end effector 16 can leverage the dexterity of the other robotic arm 116 for all movements to optimize bending of the rod 12. In one embodiment, the bending end effector 16 may incorporate a modified French bender configuration 300 as shown in FIG. 5. Similar to the holding end effector 200, the bending end effector 300 includes a housing 302 with an attachment portion 304 and a rod bending portion 306. The attachment portion 304 may include arm interface 210 and clamp 212 to secure the end effector 300 to the end of the surgical arm 116. Unlike manual French bending, bender 300 provides automatic rod bending to reduce the physical workload for the surgeon, enhance customization, and achieve optimal precision in rod bending.

As shown in FIG. 5, the bending portion 306 of the bender 300 may include a pair of bender handles or arms 310 extending from the housing 302. The bender arms 310 include a fixed center roller, mandrel, or post 312 located at the pivot of the two arms 310. One or both distal ends of the arms 310 include rollers, mandrels, or jaws 314 mounted thereon. The terms rollers, mandrels, and jaws may be used interchangeably to include tools configured to shape or bend the rod 12. In one embodiment, the rollers, mandrels, or jaws 312, 314 include cylindrical bodies that are straight and cylindrical throughout their length. Alternatively, the rollers, mandrels, or jaws 312, 314 may be tapered toward one end, conical, stepped, or have a custom shape to match specific profiles or complex geometries.

When the rod 12 contacts the mandrels 312, 314, they applying even pressure across the rod's surface. As the rod passes through the mandrels 312, 314, the rod 12 conforms to the curvature dictated by their arrangement to provide smooth consistent curves without kinking or flattening the rod 12. The distance between the mandrels 312, 314 can be adjusted to control the radius of the bend at precise angles or curves. In one embodiment, the jaws 314 may be configured to rotate around the rod 12, and the center post 312 may remain fixed to act as fixed pivot point. It will be appreciated that any of the mandrels 312, 314 may be modified to be fixed or rotational to apply the desired bending force.

In one embodiment, the rod 12 is positionable between the fixed center post 312 and the outer jaw(s) 314 along rod axis A. Application of forces to the arms 310 causes the outer jaw(s) 314 to orbit about the center post 312 so as to bend the rod 12. The rollers 312, 314 may be contoured and/or adjustable to enhance the grip of the rod 12 during the bending process. For example, the jaw(s) 314 may be adjusted to different sizes and shapes to accommodate various diameters or shapes of spinal rods 12. The bender 300 provides for precise control over the angle and radius of bends to achieve the specific rod contours needed for the individual patient. As the rod 12 is oriented in the bender 300, the actuator closes the bender handles 310 to bend the rod 12 to a given diameter and curvature of the bend.

The bender arms 310 may be automatically controlled via an actuator or motor system (e.g., AC, DC, servo, stepper). The motor(s) may be contained within the housing 302, within the surgical arms 116, or otherwise configured to control movement of the bender arm(s) 310. For example, a motor driven lead screw 316 may move the upper arm 310 relative to the lower arm 310. The lead screw 316 may include a helical thread, which interacts with a captive lead nut 318. The lead screw 316 may be aligned generally perpendicular to the lower arm 310. The proximal ends of the bending arms 310 may be captured between retention areas 320. For example, the lower arm 310 may rest in a recess or groove in the housing 302 to be fixed in position, and the upper arm 310 may interface with the captive lead nut 318. When the motor rotates, the captive lead nut 318 moves along the screw 316 to translate rotational motion into linear motion, thereby moving the upper arm 310 relative to the lower arm 310. In particular, as the lead nut 318 travels downward, the nut 318 also forces the upper arm 310 downward and toward the lower arm 310, thereby applying a bending force to the rod 12. The mechanical advantage of the bending arms 310 helps to reduce the forces required to be applied at the end effector, which enhances effectiveness while reducing the power budget. In addition, moving the bending point further away from the end effector mount 210 allows the feed mechanism to become closer to the bending mandrels 312, 314 to allow for shorter rod blanks. The motorized bending system provides for more consistent force application and finer control over the bending process compared to manual adjustments. The system may incorporate safety mechanisms, such as automatic shutdown, when resistance exceeds safe levels or to prevent damage to the rod or bender itself.

In one embodiment, the attachment portion 304 and rod bending portion 306 of the housing 302 may include separate units, resulting in a simpler and interchangeable design. For example, the attachment and rod bending portions 304, 306 may include separate housings such that the rod bending portion 306 is removably attachable to the arm attachment portion 304. The rod bending portion 306 may be secured to the attachment portion 304 with a clip, pin, screw, or other fastener 308. In this manner, the separable bending end effector 300 provides additional sterility benefits as the bending portion 306 can be sterilized independently of the attachment portion 304 of the end effector 300.

Figure 6:
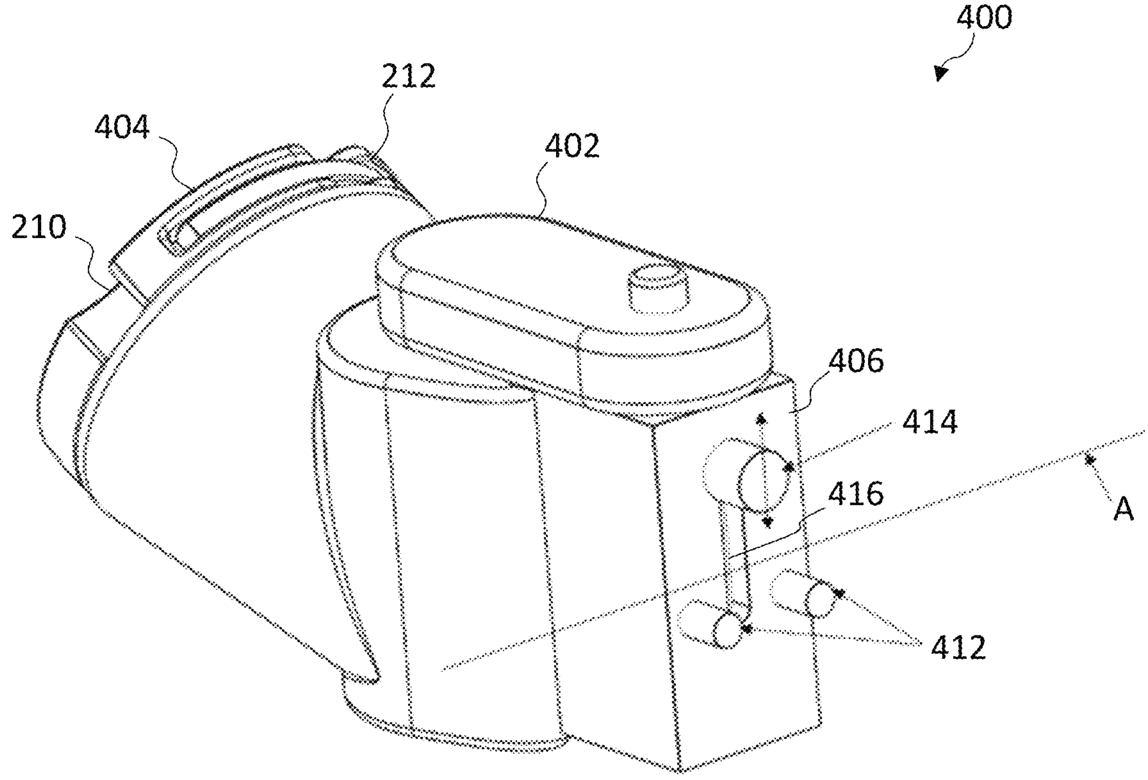
FIG. 6 shows a compact powered bending end effector according to another embodiment.

Turning now to FIG. 6, an alternative rod bender 400 is shown with a compact design. In this embodiment, the bending end effector 400 includes a housing 402 with an attachment portion 404 and a rod bending portion 406. In the same manner as end effectors 200, 300, the attachment portion 404 may include arm attachment interface 210 and clamp 212 to secure the end effector 400 to the end of the surgical arm 116. The bending portion 406 of the bender 400 includes one or more fixed mandrels 412 and a movable mandrel 414. The movable mandrel 414 may be configured to move along a slit 416, which is oriented perpendicular to the rod axis A. The mandrels 412, 414 may be similar to the rollers, mandrels, or jaws 312, 314 in end effector 300.

In one embodiment, the fixed mandrels 412 include a pair of cylindrical mandrels located on opposite sides of the bottom of slit 416. The moving mandrel 414 may have a cylindrical body with a diameter larger than the fixed mandrels 412. The diameter of the moving mandrel 414 may dictate the degree of curvature of the bend. In this embodiment, the mandrels 412, 414 are not configured to rotate, and the moving mandrel 414 is only configured to translate toward or away from the fixed mandrels 412. Although a specific configuration of mandrels 412, 414 is shown, it will be appreciated that the number, type, size, and location of mandrels, and orientation of the slit may be modified to optimize the bending performance.

The rod 12 is positionable between the movable mandrel 414 and the fixed mandrels 412 along rod axis A. As the moving mandrel 414 travels along the slit 416, the rod 12 pressed between the mandrels 412, 414, to thereby apply a bending force to the rod 12. The moving mandrel 414 may be automatically controlled with an actuator or motor to linearly translate the mandrel 414 along slit 416. The actuator or motor may be located within housing 402 or at another suitable location. The motorized system offers a consistent application of force and greater precision in controlling the bending process. The rod bender 400 is compact and self-contained with no additional pieces to install, potentially drop, or lose during the set-up process, thereby enhancing useability and efficiency.

Figure 7:
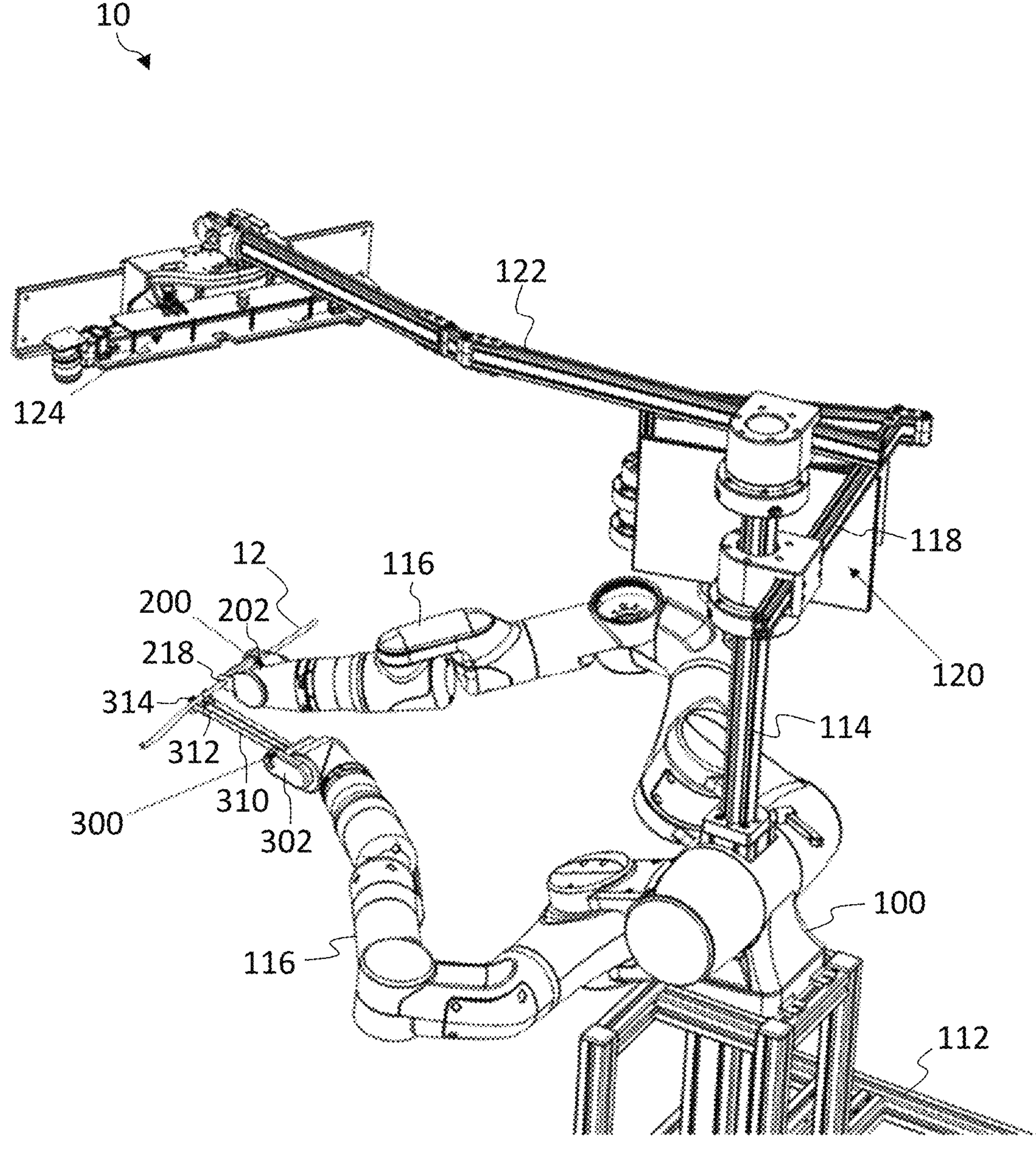
FIG. 7 shows an integrated rod bender system including a powered bender and cutter/feeder attached to the multi-arm robotic system with machine vision monitoring and verification according to one embodiment.

FIG. 7 depicts one example of the integrated rod bender system 10 including powered holder 200 as first end effector 14 and powered bender 300 as the second end effector 16 on the multi-arm robotic system 100 with machine vision monitoring and verification. It will be appreciated that powered bender 300 may be easily swapped for powered bender 400. The integrated rod bender system 10 includes powered holder 200 fitted to one surgical arm 116 and powered bender 300 fitted to the other surgical arm 116 of the robotic system 100. The fabrication process may be planned within the software of robotic system 100 and executed by the robotic system 100 in real-time. The planning workflow and in-process status may be supervised and controlled by the surgeon, for example, via the touch-screen monitor(s) 120. The entire bending procedure may be monitored with machine vision monitoring and verification, for example, via machine vision camera(s) 124.

Figure 8:
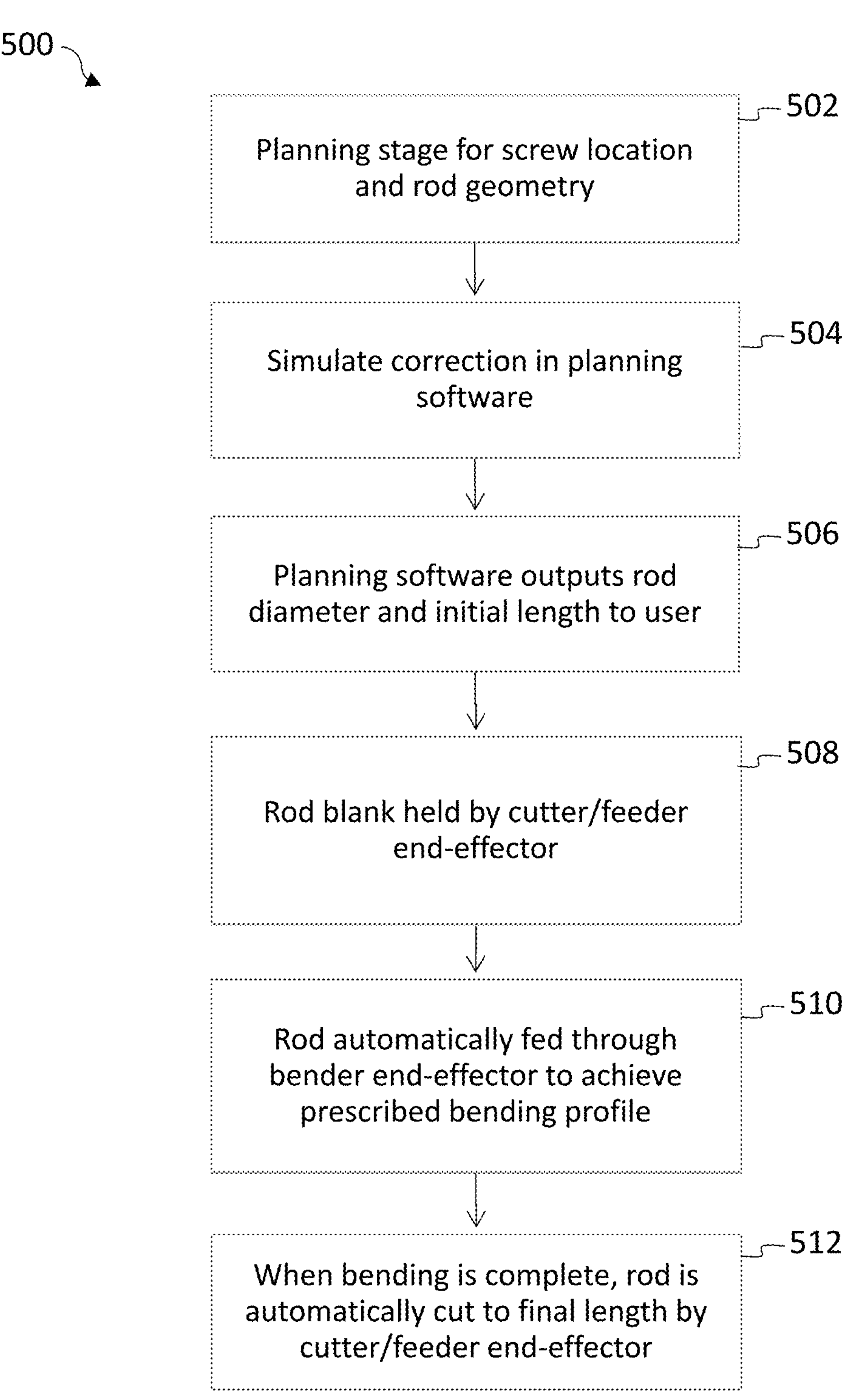
FIG. 8 is an automatic rod bending workflow using the surgical robotic system to plan and execute the rod bending process according to one embodiment.

FIG. 8 depicts a proposed workflow 500 for the rod bending process. The fabrication process may be planned and simulated within the software of the robotic system 100 or another suitable computer system. In a first step 502, the rod bending process begins in the planning stage when screw location and rod geometry is defined (e.g., via display 120). During this initial phase, the exact locations where screws will be placed may be determined, and the specific geometry and attributes (e.g., suggested diameter, material type) of the spinal rod may be defined. In a second step 504, the user can simulate correction in the planning software (e.g., via display 120). For example, the user can simulate correction with the rod to modify the rod bend accordingly from proposed or current screw locations. By engaging in these simulations, the user can observe how the rod would interact with the proposed or current screw placements and make informed decisions on necessary adjustments to the rod's curvature. The planning and simulation steps may be iterative until final screw placements are made. This dynamic approach enables the surgeon and/or system 100 to tailor the rod's shape precisely to the patient's needs before the actual bending process begins.

In one embodiment, the software may incorporate artificial intelligence (AI) to enhance the planning and simulation with AI algorithms and machine learning (ML) models. The AI system may process and analyze data, extract insights, predict trends, and learn from new data inputs over time to optimize outcomes. The AI system may continuously monitor its performance and automatically adjust or reorganize data to optimize performance. The AI system may identify patterns, anomalies, and correlations within the data that may not be otherwise apparent. It will be appreciated that any suitable AI algorithms or machine learning models may be used based on the most appropriate methodologies.

In a third step 506, the planning software outputs the appropriate starting rod diameter and length or other pertinent information to the user (e.g., via display 120). The software may provide detailed recommendations on the ideal starting diameter and length of the rod 12 based on the screw locations and desired spinal corrections. This guidance ensures that the rod 12 is of sufficient size and strength to withstand the corrective forces applied during surgery and is long enough to span the necessary vertebral segments without excess. From planning through simulation, the final output of specifications aims to streamline the rod bending process, reduce the potential for further adjustments, and enhance the overall effectiveness of the surgical intervention to achieve the best possible outcomes during the spinal surgery.

In a fourth step 508, the rod blank is held by the holding end effector 200. For example, the rod blank may first be removed from the sterile instrument tray and fed into the sterile cutter/feeder end-effector 200. The rod blank may be manually fed into the holding end effector 200 or automatically grasped by the end effector 200. For end effector 200, the rod blank may be manually fed through the top opening 216 and picked up by feed roller 220 at which point, automation takes over. In a fifth step 510, the rod blank is automatically fed through the bending end effector 300, 400. The rod 12 is automatically fed and rotated through the bender 300, 400 to achieve the prescribed bending profile, which was identified during the planning and simulation phase. It will be appreciated, however, that the plan may be updated and changed at any time throughout the procedure in real-time. Using the dexterity of the arms 116 and additional rod-centered transformations, axial and rotational, built into the feeder 200, the rod 12 is fed and rotated through the powered bender 300, 400 such that the bender 300, 400 applies bending force as prescribed by the bending profile to achieve the desired patient specific rod form.

In a final step 512, after all bending is complete, the rod 12 may be automatically cut to its final length by the holder 200. For example, the cutting mechanism 226 in the holder 200 severs excess stock and the rod 12 is ready for installation. The entire process may be continuously monitored by the machine vision camera 124 to ensure that the rod 12 is formed to specification. This enables automated, on-the-fly, corrections to compensate for spring-back and other process variation. At any suitable time, the rod 12 may notched and cut with the shearing operation at the completion of bending. For MIS rods which may require an end notch for installation, they can be fed backwards, notch side first through the bender 300, 400 to preserve the drive feature. Alternatively, the notching functionality may be integrated into the feeder/cutter end effector 200 to add the notch during cut-off. This fabrication process may be repeated as necessary, for example, to match the left and right sides of the construct.

The automated bending system eliminates manual rod bending, which is a strenuous and difficult process. The automated approach to bending removes physical workload from the surgeon, enables more complex geometries not easily achieved with hand tools, and reduces the risk of high stress areas by ensuring a smooth bend. Integration of the automated system with the multi-arm surgical robot reduces capital equipment footprint in the operating room by leveraging equipment used throughout the procedure, integrates the execution of screw placement with rod bending to one platform, and synchronizes and streamlines the data to improve accuracy. The automated bending system facilitates same day intraoperative bending so the surgeon can make final bend requirements during surgery and not before, streamlines the workflow and reduces the time of the operation by utilizing current equipment, and eliminates any sterility concerns as the robotic system is fully draped and end effectors can be sterilized in standard graphic cases. In addition, machine vision monitoring adds a safety functionality to the procedure by verifying the correct rod geometry prior to patient placement. These aspects are especially useful for deformity cases where rod geometry can be very complex.

Although several embodiments of the invention have been disclosed in the foregoing specification, it is understood that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. It is further envisioned that features from one embodiment may be combined or used with the features from a different embodiment described herein. Moreover, although specific terms are employed herein, as well as in the claims which follow, they are used only in a generic and descriptive sense, and not for the purposes of limiting the described invention, nor the claims which follow. The entire disclosure of each patent and publication cited herein is incorporated by reference in its entirety, as if each such patent or publication were individually incorporated by reference herein. Various features and advantages of the invention are set forth in the following claims.

What is claimed is:

1. An automatic rod bending system comprising:

a multi-arm surgical robotic system having a movable base station including an on-board computer, a display electronically coupled to the computer, a machine vision camera electronically coupled to the computer, and first and second surgical arms electronically coupled to the computer and movable based on commands processed by the computer;

a powered holding end effector coupled to the first surgical arm, the holding end effector having a housing defining a channel for receiving a rod therethrough, a feeder roller located adjacent to the channel such that an edge of the feeder roller is configured to contact the rod to advance the rod through the channel, a rotation roller located adjacent to the channel such that an edge of the rotation roller is configured to rotate the rod about its longitudinal axis, wherein the rotation roller is positioned perpendicular to the feeder roller; and a powered bending end effector coupled to the second surgical arm, the bending end effector having a housing with a fixed mandrel and a movable mandrel such that when the rod is positioned therebetween, the movable mandrel is configured to apply a force to bend the rod, wherein movements of the holding end effector and the bending end effector synchronize to ensure bends are made at correct locations and directions for a customized patient specific rod, wherein the bending end effector includes an upper arm and a lower arm with a fixed center post located at a pivot of the upper and lower arms, and one or both of the arms include a jaw on a distal end, such that the rod is positionable between the fixed center post and the jaw.

2. The system of claim 1, wherein the holding end effector further includes cutoff shears located at an exit of the channel.

3. The system of claim 2, wherein the cutoff shears include a pair of blades that slide past each other to automatically cut the rod to a desired final length.

4. The system of claim 1, wherein the holding end effector further includes a notch cutter with a cutting head configured to notch the rod.

5. The system of claim 1, wherein the upper and lower arms are automatically controlled by a motor driven lead screw.

6. The system of claim 5, wherein the motor driven lead screw interacts with a captive lead nut to move the upper arm relative to the lower arm.

7. The system of claim 6 wherein a proximal end of the lower arm rests in a groove in the housing of the bending end effector in a fixed position, and a proximal end of the upper arm interfaces with the captive lead nut such that when the captive lead nut travels downward, the nut forces the upper arm downward, thereby applying a bending force to the rod.

8. The system of claim 1, wherein the bending end effector includes a pair of fixed mandrels and the movable mandrel is configured travel along a slit in the housing.

9. The system of claim 8, wherein the slit is oriented perpendicular to the longitudinal axis of the rod when positioned between the fixed and movable mandrels.

10. The system of claim 1, wherein the holding and bending end effectors are powered by one or more electric motors, which are controlled by the robotic system.

11. A process workflow for intraoperative rod bending comprising:

planning screw location and rod geometry using a surgical robotic system having a machine vision camera;

simulating spinal correction using the surgical robotic system to determine a prescribed bending profile for a rod based on proposed or current screw locations;

outputting rod diameter and initial rod length defined by the surgical robotic system to a user;

inserting a rod blank into a powered holding end effector positioned on a first arm of the surgical robot system having a housing defining a channel for receiving the rod blank therethrough, a feeder roller for advancing the rod blank through the channel, and a rotation roller for rotating the rod blank about its longitudinal axis;

automatically feeding and rotating the rod blank through a powered bending end effector positioned on a second arm of the surgical robot system having a housing with a fixed mandrel and a movable mandrel with the rod blank positioned therebetween, and moving the movable mandrel to bend the rod blank to the prescribed bending profile for the rod; and automatically cutting the rod to length by the powered holding end effector, wherein a pivot axis of the first arm and a pivot axis of the second arm are generally colinear.

12. The process of claim 11, wherein the entire process is continuously monitored by the machine vision camera to ensure that the rod is formed according to the prescribed bending profile.

13. The process of claim 11, wherein the rod bending occurs intraoperatively during surgery.

14. The process of claim 11, wherein the robotic system is configured to make automated, on-the-fly, corrections throughout the process.

15. The process of claim 11, further comprising installing screws with the surgical robotic system.

16. The process of claim 15, wherein the planning and simulation steps are iterative until final screw placements are made.

17. The process of claim 11, further comprising notching the rod with the powered holding end effector.

18. The process of claim 11, further comprising replacing one or both of the end effectors to perform different functions during the surgical procedure.

19. An automatic rod bending system for use with a multi-arm surgical robotic system with machine vision monitoring and verification, the rod bending system comprising:

a powered holding end effector coupled to a first surgical arm of the multi-arm surgical robotic system, the holding end effector having a housing defining a channel extending from an entry point to an exit point for receiving a rod therethrough along a longitudinal rod axis, a feeder roller located adjacent to the channel such that an edge of the feeder roller is configured to automatically advance the rod through the channel, a rotation roller located adjacent to the channel such that an edge of the rotation roller is configured to automatically rotate the rod about the rod axis, wherein the rotation roller is positioned perpendicular to the feeder roller, a notch cutter positioned beneath the rotation roller and adjacent to the channel such that a cutting head of the notch cutter is configured to automatically notch the rod, and cutoff shears located near the exit point of the channel to automatically cut the rod to a desired length; and a powered bending end effector coupled to a second surgical arm of the multi-arm surgical robotic system, the bending end effector having a housing and a pair of bender arms with a fixed center post located at a pivot of the bender arms, one or more jaws mounted on distal ends of the bender arms, and a motor driven lead screw which interacts with a captive lead nut to move one of the bender arms, wherein the rod is positionable between the fixed center post and the one or more jaws along the rod axis, and application of force to the bender arms causes the one or more jaws to orbit about the center post, thereby applying a bending force to the rod, wherein the rod is configured to be automatically fed, rotated, and bent into a complex three-dimensional geometry based on a planned and simulated intraoperative rod plan from the surgical robotic system, to thereby produce a customized patient specific rod in real-time.

* * * * *